US010533963B2

(12) United States Patent
Lin et al.

(10) Patent No.: US 10,533,963 B2

(45) Date of Patent: Jan. 14, 2020

(54) BIOSENSOR DEVICE

(71) Applicant: Mobiosense Corp., Taipei (TW)

(72) Inventors: Chih-Ting Lin, Taipei (TW); Yu-Hao Chen, Taipei (TW); Sheng-Yeh Chou, Taipei (TW)

(73) Assignee: MOBIOSENSE CORP., Taipei (TW)

( * ) Notice: Subject to any disclaimer, the term of this patent is extended or adjusted under 35 U.S.C. 154(b) by 358 days.

(21) Appl. No.: 15/401,123

(22) Filed: Jan. 9, 2017

(65) Prior Publication Data

US 2018/0195991 A1 Jul. 12, 2018

(51) Int. Cl.

| | |
|---|---|
| ***G01N 27/00*** | (2006.01) |
| ***G01N 15/06*** | (2006.01) |
| ***G01N 33/00*** | (2006.01) |
| ***G01N 33/48*** | (2006.01) |
| ***G01N 27/12*** | (2006.01) |

(52) U.S. Cl.

CPC .................................. *G01N 27/125* (2013.01)

(58) Field of Classification Search

CPC ........ G01N 27/00; G01N 15/06; G01N 33/00; G01N 33/48

USPC ..................... 422/68.1, 82.01, 82.02; 436/43

See application file for complete search history.

(56) References Cited

U.S. PATENT DOCUMENTS

| | | | | |
|---|---|---|---|---|
| 6,528,020 B1 * | 3/2003 | Dai | B82B 1/00 | 422/82.02 |
| 6,703,132 B1 * | 3/2004 | Yasuda | B81C 1/00896 | 324/244 |
| 6,732,583 B1 * | 5/2004 | Yasuda | G01F 1/6845 | 324/207.21 |
| 7,301,199 B2 * | 11/2007 | Lieber | B82Y 10/00 | 257/327 |
| 8,232,584 B2 * | 7/2012 | Lieber | A61B 5/14546 | 257/253 |
| 2006/0006463 A1 | 1/2006 | Islam et al. | | |
| 2011/0193183 A1 * | 8/2011 | Agarwal | B01J 19/0046 | 257/414 |
| 2012/0077680 A1 | 3/2012 | Berggren et al. | | |
| 2012/0235647 A1 * | 9/2012 | Chung | G01P 15/11 | 322/3 |
| 2012/0235694 A1 * | 9/2012 | Asano | G01P 15/0802 | 324/705 |

FOREIGN PATENT DOCUMENTS

CN 103842817 A 6/2014

* cited by examiner

*Primary Examiner* — Brian J. Sines

(74) *Attorney, Agent, or Firm* — Bacon & Thomas, PLLC

(57) ABSTRACT

A biosensor device includes a substrate, an oxide layer and a sensing wire. The oxide layer is disposed on the substrate. The sensing wire is disposed on the oxide layer. The sensing wire is provided to receive target biomolecules. The sensing wire includes at least one first section extending along a first direction and at least one second section extending along a second direction. The at least one first section is continuous with the at least one second section. The first direction is different from the second direction. The sensing wire has a width and a total length and a ratio of the total length to the width is larger than 500.

15 Claims, 4 Drawing Sheets

3
39
37
371 371
38
35
34
36
33
32 31

BIOSENSOR DEVICE

BACKGROUND OF THE INVENTION

1. Field of the Invention

The present invention relates to a biosensor, and more particularly, to a biosensor device.

2. Description of Related Art

Biosensors are expected for measurements in biological features such as corpuscles, proteins, carbohydrates, antibodies or metal ions. Biosensors are advantageous for their high specificity, high sensitivity and high selectivity, and are applicable in the fields of medicine, biological technology, food, agriculture and environment monitoring.

FIG. 1 shows a prior sensor device 1, in which a sensing wire 11 is used to detect the target biomolecules. However, due to manufacturing tolerances, such as non-uniformity of etching, non-uniformity of coating or non-uniformity of doping, there may be some defects 12 existing in the sensor device 1. As shown in FIG. 1, the defects 12 also exist in a part of the sensing wire 11, which will cause measurement inaccuracy in sensing for the sensor device 1.

FIG. 2 shows another prior sensor device 2, in which a plurality of sensing wires 21 are used to detect the target biomolecules, and thus some of the sensing wires 21 can be kept away from the defects 12. However, in order to receive the sensing signals generated by the sensing wires, a multiplexer 22 is required for selecting the sensing signals to be outputted. The multiplexer 22 and its wiring will increase the complexity and the cost for manufacturing the sensor device 2.

Therefore, it is desirable to provide an improved biosensor device to mitigate or obviate the aforementioned problems.

SUMMARY OF THE INVENTION

An object of the present invention is to provide a biosensor device which can reduce the influence of manufacturing variation and improve coefficient of variation in measurements.

Another object of the present invention is to provide a biosensor device which can reduce the complexity and the cost for manufacturing the biosensor device.

To achieve the objects, the biosensor device according to the present invention includes a substrate, an oxide layer and a sensing wire. The oxide layer is disposed (deposited) on the substrate. The sensing wire is disposed (deposited) on the oxide layer. The sensing wire is provided to receive target biomolecules. The sensing wire includes at least one first section extending along a first direction and at least one second section extending along a second direction, the at least one first section is continuous with the at least one second section, and the first direction is different from the second direction. The sensing wire has a width and a total length, and the ratio of the total length to the width is larger than 500.

Other objects, advantages, and novel features of the invention will become more apparent from the following detailed description when taken in conjunction with the accompanying drawings.

DETAILED DESCRIPTION OF THE PREFERRED EMBODIMENT

Different embodiments according to the present invention are provided in the following description. It is to be understood that the embodiments are not meant to be limiting. Other embodiments can be utilized by arranging, substituting, combining, separating, and designing the features according to the present invention.

Figure 3:
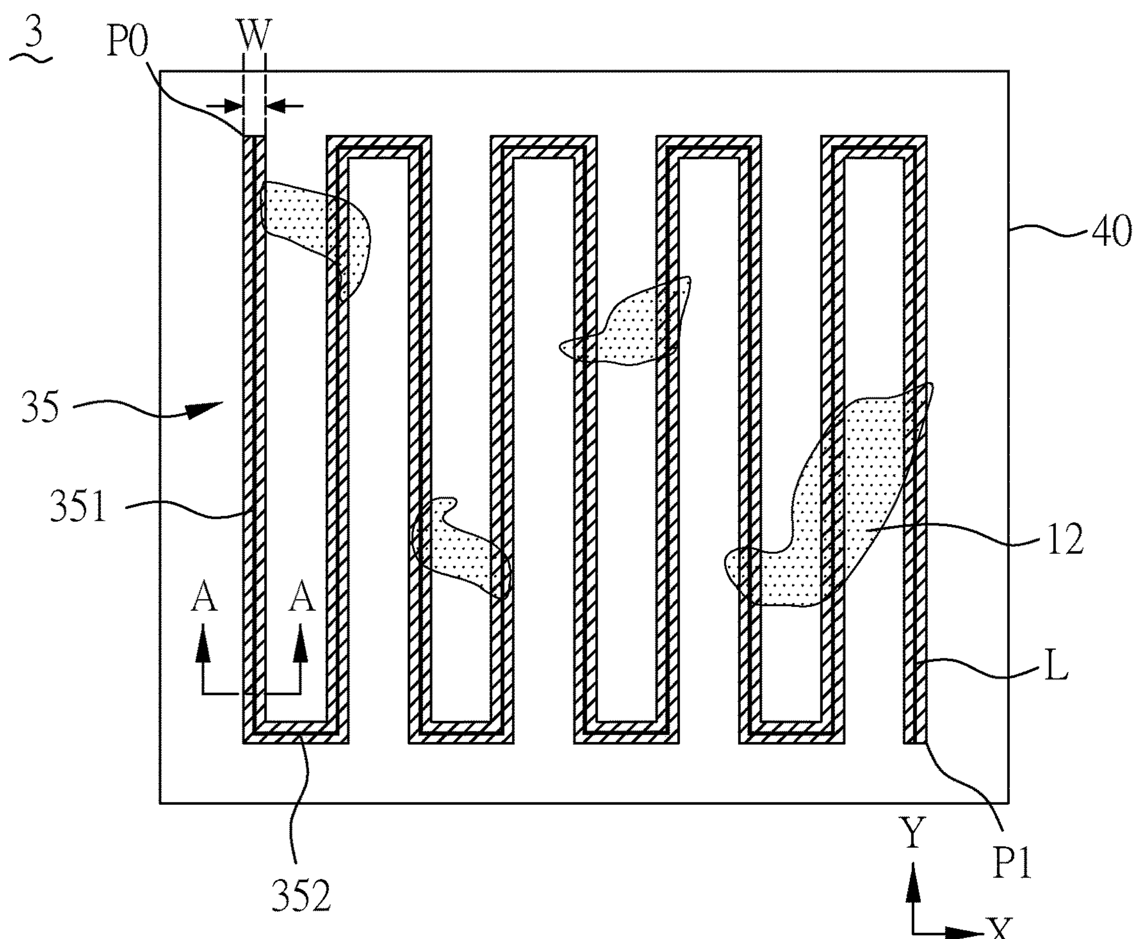
FIG. 3 shows a top view of the biosensor device according to one embodiment of the present invention.

FIG. 3 shows a top view of the biosensor device 3 according to one embodiment of the present invention. As shown in FIG. 3, there is a sensing wire 35 extending along a zigzag path in an interface area 40 of the biosensor device 3.

Figure 4:
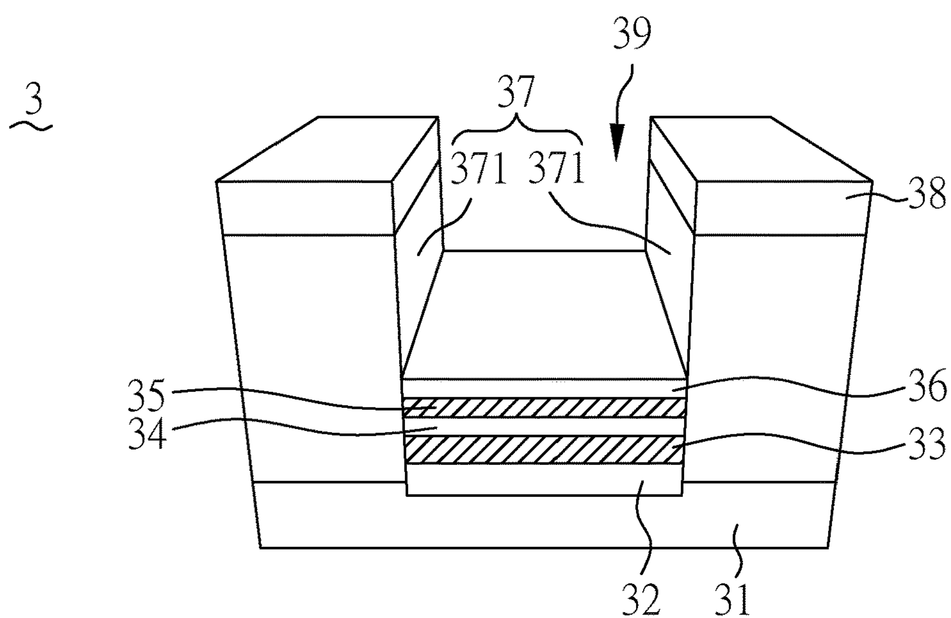
FIG. 4 shows a perspective view of the structure of the biosensor device according to the present invention.

To further describe the details of the biosensor device 3, FIG. 4 shows a perspective view of the structure of the biosensor device 3 according to the present invention. In particular, FIG. 4 shows a cross-sectional view from A-A line in FIG. 3. As shown in FIG. 4, the biosensor device 3 includes a substrate 31, a field oxide layer 32, a conductive layer 33, an oxide layer 34, a sensing wire 35, a coating layer 36, a wall layer 37 and a passivation layer 38.

The substrate 31 can be made of semiconductor materials such as Si, Ge, SiC, GaAs, GaP, InP, InAs, InSb, SiGe, GaAsP, AlInAs, AlGaAs, GaInAs, GaInP, GaInAsP, or the combinations thereof, and it is preferred to be made of Si.

The field oxide layer 32 is formed on the substrate 31. It can be made of dielectric materials such as silicon oxide, silicon nitride, silicon oxynitride, dielectric with a high dielectric constant (high-k), or the combinations thereof.

The conductive layer 33 is formed on the field oxide layer 32. It can be made of semiconductor materials as previously described for the substrate 31, and it is preferred to be made of $WSi_x$. Alternatively, the conductive layer 33 can be formed of conductive materials such as Cu, W, Ti, Ta, Cr, Pt, Ag, Au, TiN, TaN, NiSi or CoSi.

The oxide layer 34 is formed on the conductive layer 33. It can be made of the dielectric materials as previously described for the field oxide layer 32.

The sensing wire 35 is formed on the oxide layer 34. It can be made of the semiconductor materials as previously described for the substrate 31. In the case of silicon, it can be made of crystalline silicon (c-Si), polycrystalline silicon (poly-Si) and amorphous silicon (a-Si). Furthermore, in this case, the sensing wire 35 is doped with N-type dopants (N+, N or N−) to increase its conductivity. In other cases, it can be doped with P-type dopants (P+, P or P−).

In general, the sensing wire 35 is connected to a first conducting portion (not shown) at one end and a second conducting portion (not shown) at the other end. Furthermore, the conducting portions are connected to the electrodes, so that the sensing signal generated by the sensing wire 35 can be outputted to an additional circuit (not shown), for example, a comparator, an amplifier or a filter.

The conducting portions can be formed simultaneously with the sensing wire 35, and/or of the same material of the sensing wire 35, and/or at the same layer of the sensing wire 35 on the oxide layer 34. Each of the conducting portions has a width larger than the width W (as shown in FIG. 4) of the sensing wire 35 for reducing the on-state resistance.

The coating layer 36 is optionally coated on the sensing wire 35 for capturing (immobilizing) the target biomolecules. The coating layer 36 includes organic materials such as proteins, haptens, peptides, polypeptides, antibodies, polynucleotides or crosslinkers, such as chemicals for silanization. In other cases, the coating layer 36 can be omitted.

In manufacturing, the wall layer 37 is formed on the substrate 31, and is covered by the passivation layer 38. The wall layer 37 and the passivation layer 38 are etched to form a well 39 until the well 39 reaches the substrate 31. The field oxide layer 32, the conductive layer 33, the oxide layer 34, the sensing wire 35, and the coating layer 36 are then formed in turn on the substrate 31 in the well 39.

It can be seen that the wall layer 37 is substantially formed by a plurality of walls 371 which define the well 39 as well as the path of the sensing wire 35 (as shown in FIG. 3).

The wall layer 37 can be a multilayer interconnection (MLI) structure with interlayer dielectric (ILD). Some additional circuits in communication with the biosensor device 3 can be included in the wall layer 37. Those additional circuits may be used to process the sensing signal.

The passivation layer 38 is used to protect the wall layer 37. In some cases, the passivation layer 38 can be omitted.

In operation, the sensing wire 35 is used to receive target biomolecules, such as corpuscles, proteins, carbohydrates, antibodies or metal ions. The target biomolecules will induce an electric field on the sensing wire 35, and the electric field will then induce charges occurring in the sensing wire 35. The induced charges will affect resistance of the sensing wire 35. Accordingly, a sensing signal is generated by the sensing wire 35. With the sensing signal, the existence, the amount or the type of target molecules can be determined.

Referring back to FIG. 3, the interface area 40 is a rectangular area, so that the layout of the biosensor device 3 can be simplified, and the manufacture of the biosensor device 3 can be compatible with the standard CMOS fabrication.

As shown in FIG. 3, the sensing wire 35 includes a plurality of first sections 351 extending along a first direction (X-axis direction) and a plurality of second sections 352 extending along a second direction (Y-axis direction). The first direction is different from the second direction, namely, they are not parallel to each other. In this case, the first direction is perpendicular to the second direction. Further, each of the second sections 352 connects two adjacent ends of two adjacent first sections 351.

Figure 2:
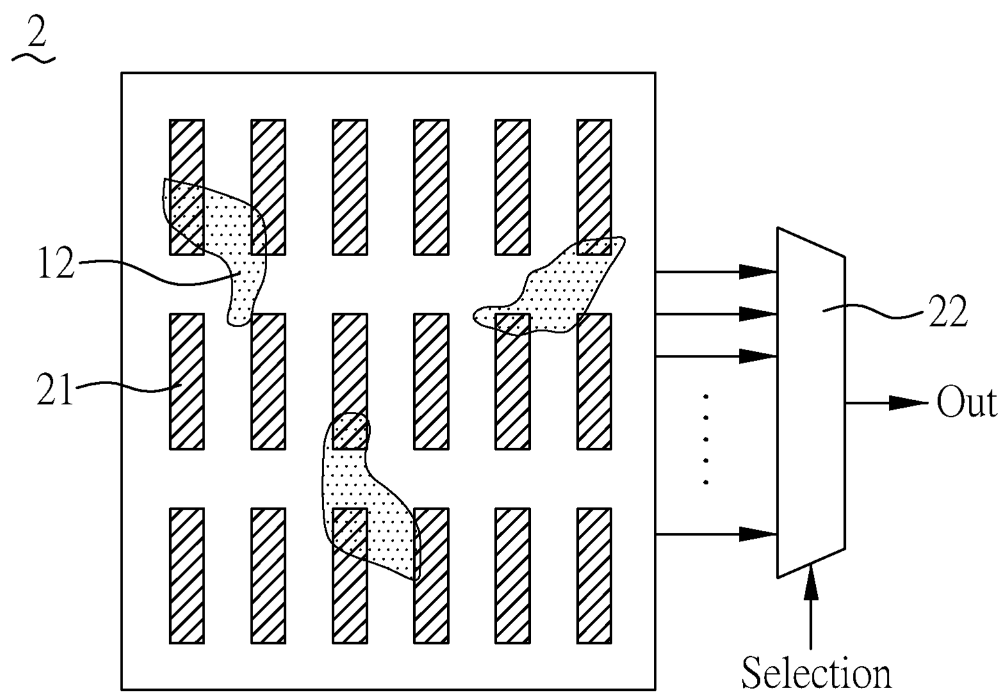
FIG. 2 shows another prior sensor device.

It is noted that, the sensing wire 35 extends continuously in one path without any branch. Thus, compared to the prior sensor device 2 as shown in FIG. 2, the biosensor device 3 according to the present invention does not require a multiplexer for selection.

The sensing wire 35 is preferred to extend all over the interface area 40 so as to increase the efficient sensing area. As shown in FIG. 3, the sensing wire 35 extends at least through the center, the four edges and the four corners of a rectangular interface area 40.

Since the sensing wire 35 includes a plurality of first sections 351 extending along a first direction (X-axis direction) and a plurality of second sections 352 extending along a second direction (Y-axis direction), it can extend horizontally to realize a zigzag path.

Figure 1:
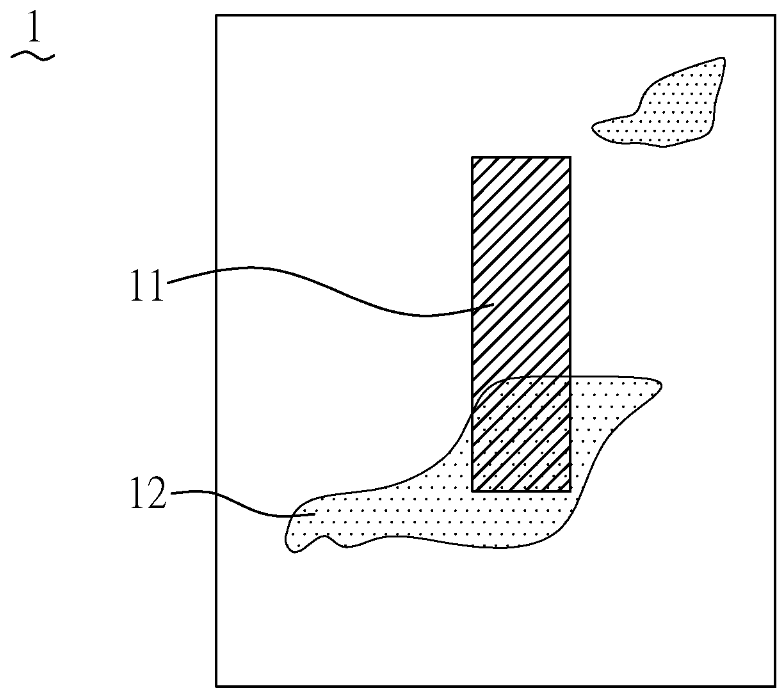
FIG. 1 shows a prior sensor device.

Since the defects can be distributed everywhere with equal possibility, the possibility that the sensing wire 35 encounters the defects is sufficiently spread with the zigzag path. Furthermore, since one section that encounters the defects is continuous with one section that avoids the defects, the respective sensing signals will be mixed and then be averaged. Thus, the influence of the defects can be alleviated. It is beneficial to realize a zigzag path for the sensing wire 35 compared to the prior sensor device 1 as shown in FIG. 1.

Besides, the sensing wire 35 can obtain a better sensing performance if its total length is sufficient long. For quantitative analysis, a width W and a total length L of the sensing wire 35 are defined in FIG. 3. It is noted that, the total length L starts at P0 at the top-left of the interface area 40, goes along the sensing wire 35, and ends at P1 at the bottom-right of the interface area 40.

Based on experimental results, it shows that the sensing wire 35 can obtain a better sensing performance if the ratio of the total length L to the width W, that is L/W. Preferably, the sensing wire 35 has a width W of 50 nm and a total length L of larger than 25 um, and thus L/W is larger than 500. Preferably, the sensing wire 35 has a width W of 50 nm and a total length L of larger than 50 um, and thus L/W is larger than 1000.

FIGS. 5 to 8 show other embodiments of the biosensor device 3 according to the present invention, which illustrate that several kinds of paths are possible in addition to the zigzag path shown in FIG. 3.

Figure 5:
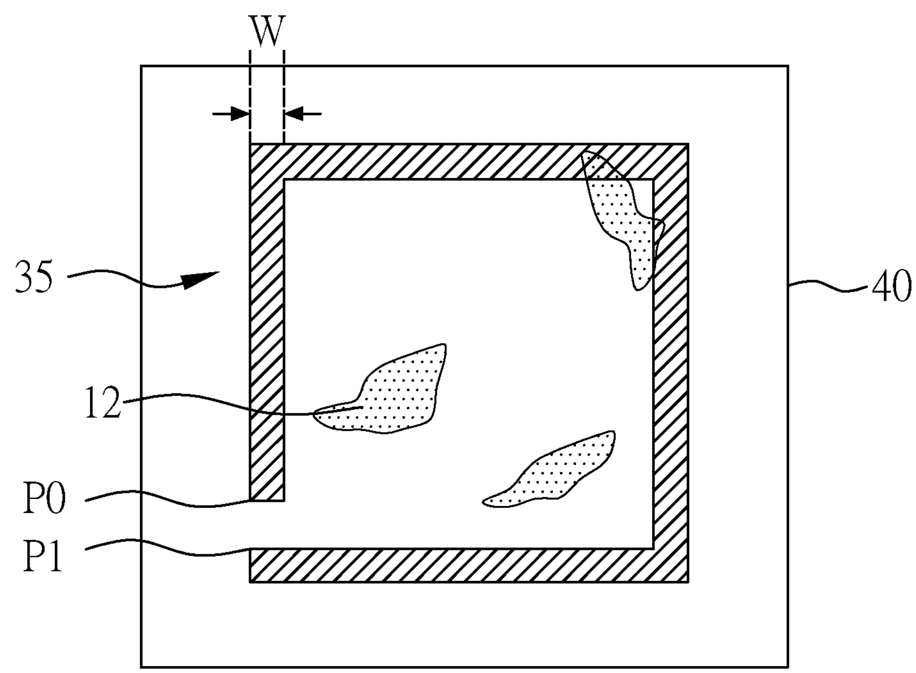
FIGS. 5 to 8 show top views of the biosensor devices according to other embodiments of the present invention.

FIG. 5 shows a sensing wire 35 extending along a ring-like path. The ring-like path goes through the four edges of the interface area 40 for only one round, and the ratio of the total length L (which starts at P0, goes along the sensing wire 35, and ends at P1) of the sensing wire 35 to the width W of the sensing wire 35 is larger than 500. Due to L/W>500, the sensing wire 35 can still provide a better sensing performance compared to the prior art. A circular path may also be realized if the manufacturing allows.

Figure 6:
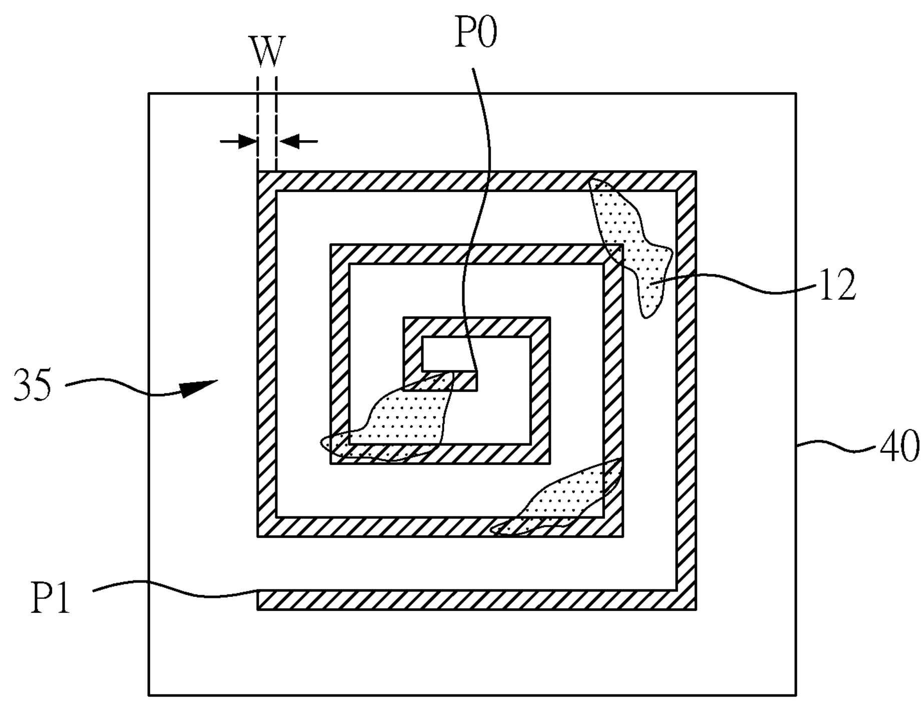

FIG. 6 shows a sensing wire 35 extending along a spiral path, which can be regarded as an improvement based on the embodiment of FIG. 5. As shown in FIG. 6, one end of the sensing wire 35 is at the center of the interface area 40, and the other end the sensing wire 35 is at a corner of the interface area 40, while the ratio of the total length L (which starts at P0, goes along the sensing wire 35, and ends at P1) of the sensing wire 35 to the width W of the sensing wire 35 is larger than 500.

Figure 7:
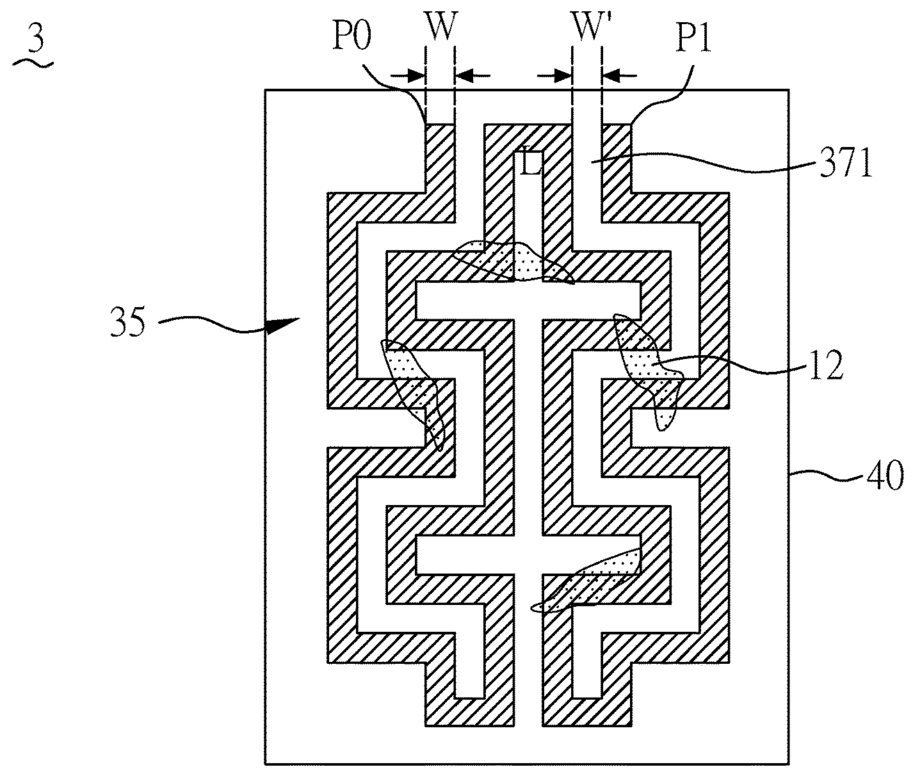

FIG. 7 shows a sensing wire 35 extending along a symmetrical path. The first (left-side) sub-path is symmetrical to the second (right-side) sub-path, and both of them are zigzag paths, and the ratio of the total length L (which starts at P0, goes along the sensing wire 35, and ends at P1) of the sensing wire 35 to the width W of the sensing wire 35 is larger than 500. Each of the walls 371 has a width W' equal to the width W of the sensing wire 35.

Figure 8:
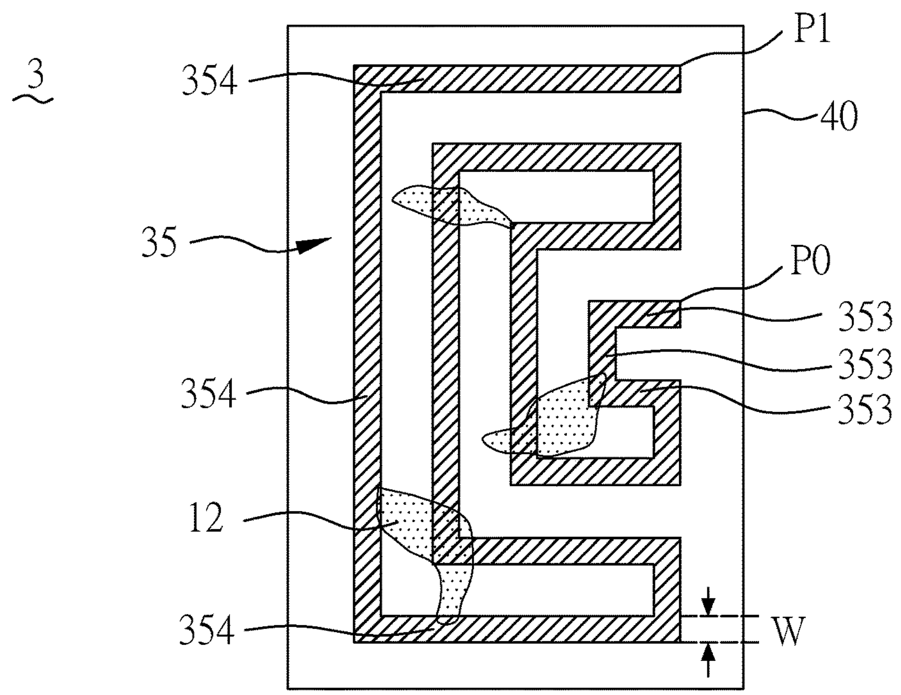

FIG. 8 shows a sensing wire 35 extending along a specific path, which includes a plurality of short sections 353 connected to each other, and a plurality of long sections 354 connected to each other. The sensing wire 35 starts at one of the short sections 353 and ends at one of the long sections 354, and the ratio of the total length L (which starts at P0, goes along the sensing wire 35, and ends at P1) of the sensing wire 35 to the width W of the sensing wire 35 is larger than 500.

Hence, different embodiments has been provided for implementing a biosensor device which can reduce the influence of manufacturing variation and improve coefficient of variation in measurements, as well as reduce the complexity and the cost for manufacturing the biosensor device.

Although the present invention has been explained with the aforementioned embodiment, it is to be understood that many other modifications and variations can be made without departing from the spirit and scope of the invention as hereinafter claimed.

What is claimed is:

1. A biosensor device, comprising:

a substrate;

an oxide layer disposed on the substrate; and a sensing wire disposed on the oxide layer adapted for receiving target biomolecules, and including at least one first section extending along a first direction and at least one second section extending along a second direction, the at least one first section being continuous with the at least one second section, the first direction being different from the second direction, wherein the sensing wire has a width and a total length and a ratio of the total length to the width is larger than 500;

wherein the sensing wire extends through a center, four edges and four corners of a rectangular interface area; and wherein the sensing wire is disposed in a well surrounded by a wall layer.

2. The biosensor device as claimed in claim 1, wherein the first direction is perpendicular to the second direction.

3. The biosensor device as claimed in claim 1, wherein the sensing wire extends along one path without any branch.

4. The biosensor device as claimed in claim 1, wherein the sensing wire has a plurality of the first sections and a plurality of the second sections, and each of the second sections connects two adjacent first sections.

5. The biosensor device as claimed in claim 1, wherein the sensing wire extends along a zigzag path.

6. The biosensor device as claimed in claim 1, wherein the sensing wire extends along a spiral path.

7. The biosensor device as claimed in claim 1, wherein the sensing wire extends along a path with a first sub-path symmetrical to a second sub-path.

8. The biosensor device as claimed in claim 1, wherein the sensing wire extends along a zigzag path with a first sub-path symmetrical to a second sub-path.

9. The biosensor device as claimed in claim 1, wherein the sensing wire extends along a path defined by a plurality of walls, and each of the walls has a width equal to the width of the sensing wire.

10. The biosensor device as claimed in claim 1, wherein the sensing wire includes a plurality of short sections connected to each other, and a plurality of long sections connected to each other.

11. The biosensor device as claimed in claims 1, wherein the ratio of the width to the total length is 1000.

12. The biosensor device as claimed in claims 1, further comprising a coating layer coated on the sensing wire.

13. The biosensor device as claimed in claims 12, wherein the coating layer is formed of organic materials.

14. The biosensor device as claimed in claim 1, further comprising a first conducting portion and a second conducting portion disposed on the oxide layer, the first conducting portion being connected to one end of the sensing wire, the second conducting portion being connected to the other end of the sensing wire.

15. The biosensor device as claimed in claim 14, wherein each of the first conducting portion and the second conducting portion has a width larger than the width of the sensing wire.

* * * * *